(12) United States Patent
Russett, III

(10) Patent No.: US 10,703,560 B2
(45) Date of Patent: Jul. 7, 2020

(54) ADULT TOY CONCEALING CONTAINER

(71) Applicant: Richard Charles Russett, III, Memphis, TN (US)

(72) Inventor: Richard Charles Russett, III, Memphis, TN (US)

( * ) Notice: Subject to any disclaimer, the term of this patent is extended or adjusted under 35 U.S.C. 154(b) by 87 days.

(21) Appl. No.: 15/807,490

(22) Filed: Nov. 8, 2017

(65) Prior Publication Data
US 2018/0065797 A1 Mar. 8, 2018

Related U.S. Application Data

(63) Continuation-in-part of application No. 14/697,668, filed on Apr. 28, 2015, now abandoned.

(51) Int. Cl.
| | |
|---|---|
| *B65D 85/00* | (2006.01) |
| *A61L 2/26* | (2006.01) |
| *A61L 2/10* | (2006.01) |
| *B65D 85/20* | (2006.01) |
| *B65D 25/10* | (2006.01) |
| *A61H 19/00* | (2006.01) |
| *B65D 81/32* | (2006.01) |

(52) U.S. Cl.
CPC .............. *B65D 85/70* (2013.01); *A61H 19/44* (2013.01); *A61L 2/10* (2013.01); *A61L 2/26* (2013.01); *B65D 81/3205* (2013.01); *B65D 85/20* (2013.01); *A61H 2201/0107* (2013.01); *A61H 2201/0138* (2013.01); *A61H 2201/0153* (2013.01); *A61H 2201/0157* (2013.01); *A61L 2202/11* (2013.01); *A61L 2202/122* (2013.01); *A61L 2202/182* (2013.01); *B65D 25/10* (2013.01)

(58) Field of Classification Search
CPC ........ A61H 19/00; A61H 19/30; A61H 19/32; A61H 19/40; A61H 21/00; A61H 19/34; A61H 19/44; A61H 23/02; A61L 2/10; A61L 2/26; B65D 85/70; B65D 25/10; B65D 85/54; B65D 81/3205; B65D 85/20
USPC ....... 206/457, 234, 69, 363; 600/38; 601/46, 601/57, 49
See application file for complete search history.

(56) References Cited

U.S. PATENT DOCUMENTS

| | | | | |
|---|---|---|---|---|
| 3,459,294 | A * | 8/1969 | Crosman | B65D 11/00 206/457 |
| 6,343,612 | B1 * | 2/2002 | Dahl | A61L 2/18 134/117 |
| 8,596,480 | B2 * | 12/2013 | Arjomand | B65D 7/04 220/4.01 |
| 2008/0237233 | A1 * | 10/2008 | Choi | A47G 19/2266 220/212.5 |

(Continued)

*Primary Examiner* — Rafael A Ortiz
(74) *Attorney, Agent, or Firm* — David J. Kreher

(57) ABSTRACT

In the military, colleges, and university privacy can be at a minimum. Even around the home, there are children and visitors. In each of these environments, other individuals finding one's adult toy can lead to embarrassment. The present disclosure is a container designed to store an individual's adult toy in what appears to be a common household item such as a shampoo bottle, conditioner bottle or soap dispenser. These containers can then be transported to and from the bathroom there the adult toy can be used or cleaned in private and if the container is observed, questions will not be raised as to the contents of the container.

1 Claim, 4 Drawing Sheets

(56) References Cited

U.S. PATENT DOCUMENTS

| | | | | |
|---|---|---|---|---|
| 2011/0049391 A1* | 3/2011 | Yang | ............................ | A61L 2/10 250/492.1 |
| 2011/0100865 A1* | 5/2011 | Brink | ...................... | A61C 19/02 206/581 |
| 2013/0320037 A1* | 12/2013 | Chovanec | ............ | B65D 81/365 222/78 |
| 2015/0076363 A1* | 3/2015 | Wen | ............................ | A61L 2/10 250/455.11 |

\* cited by examiner

ADULT TOY CONCEALING CONTAINER

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC

Not Applicable

DESCRIPTION

Field of the Invention

This disclosure relates to the field of storing and properly maintaining one's adult toy while disguising the container into which the adult toy is held, so that if the container is observed, the observer does not realize an adult toy is contained therein.

Background of the Invention

This disclosure relates to preserving the modesty and health of society. In the military and colleges and university privacy can be at a minimum. Even around the home, there are children and visitors. In each of these environments, other individuals finding ones adult toy can lead to embarrassment. The present disclosure is a container designed to store an individual's adult toy in what appears to be a common household item such as a shampoo bottle, conditioner bottle or soap dispenser. These containers can then be transported to and from the bathroom there the adult toy can be used or cleaned in private and if the container is observed, questions will not be raised as to the contents of the container.

The inventor has not found any attempts to create a similar invention.

SUMMARY OF THE INVENTION

The present disclosure reveals a container with the appearance of but not limited to a shampoo bottle, a conditioner bottle, or a soap dispenser, for the purpose of concealing an adult toy inside the container. The container has several different embodiments to further aid in the disguise of the container while also facilitating the hygienic use of adult toy.

In one embodiment, the bottom portion of the container is also a storage compartment for disposable wipes which can be used to wash the adult toy.

In another embodiment the top portion of the container comprises a hollow compartment into which shampoo, conditioner or soap and dispense.

The main compartment may also comprise a uv light to facilitate the disinfecting of the adult toy.

AMENDED BRIEF DESCRIPTION OF THE SEVERAL VIEWS OF THE DRAWING

FIG. 1 is a view of the first embodiment of the container including a bottom portion, a main compartment and a top portion;

FIG. 2 first embodiment of the bottom portion of the container;

AMENDED DETAILED DESCRIPTION OF THE INVENTION

Figure 1:
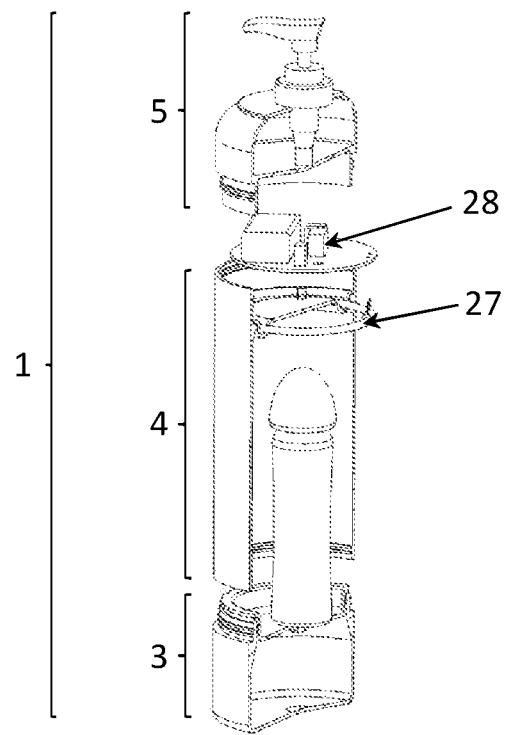
Figure 2:
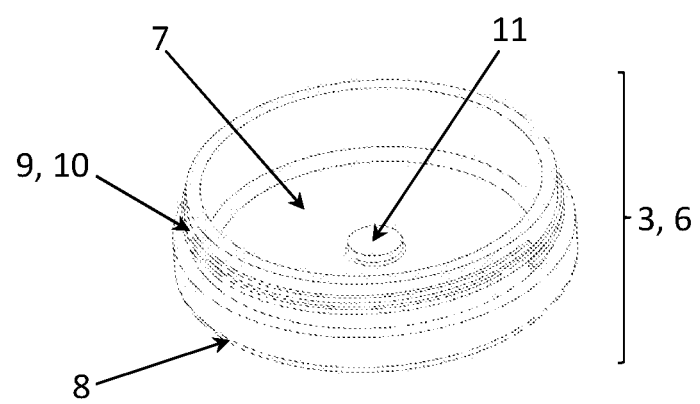
Figure 3:
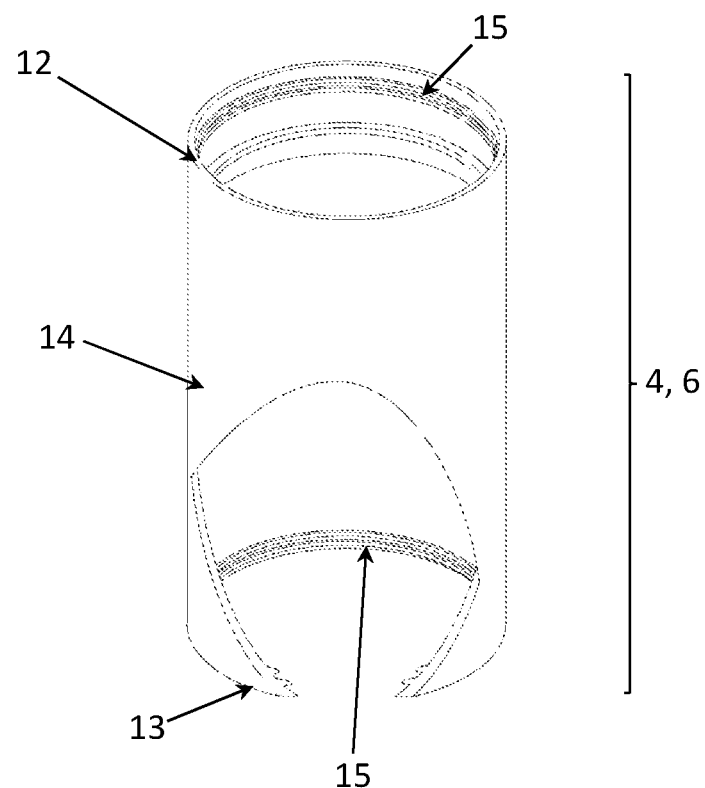
FIG. 3 is a view of the second embodiment of the bottom portion of the container including the upper part with the opening and the storage means.
Figure 4:
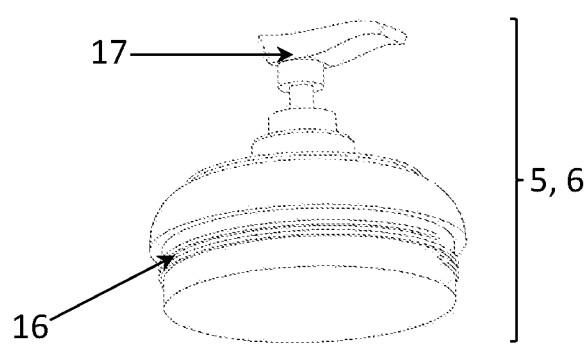
FIG. 4 is a view of the main compartment as displayed as a cylinder and also revealing the receiver of the lower edge and the receiver of the upper edge.
Figure 5:
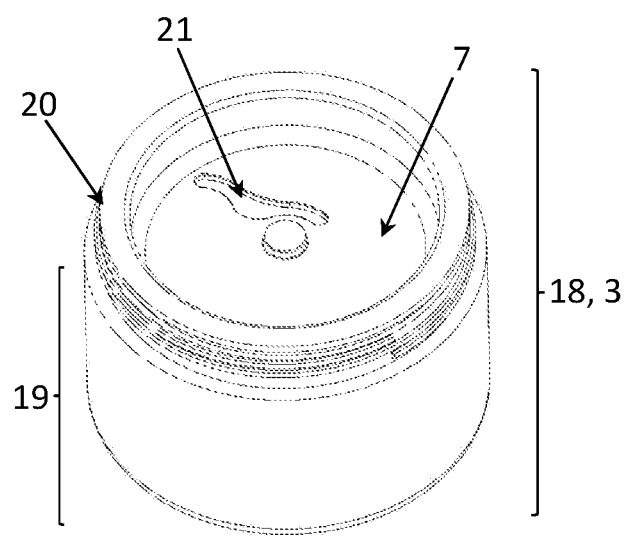
FIG. 5 is a view of the top portion of the container with the opening as a flip top.
Figure 6:
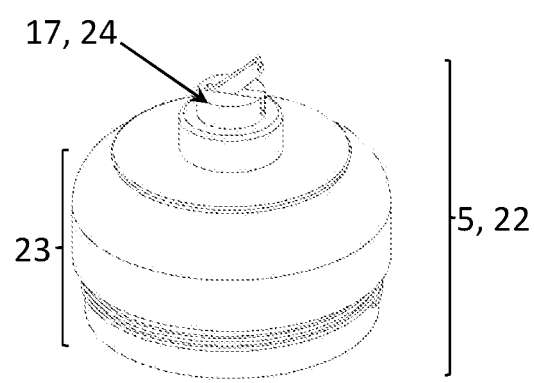
FIG. 6 is a view of the top portion of the container indicating the hollow compartment and where the opening is a flip top.
Figure 7:
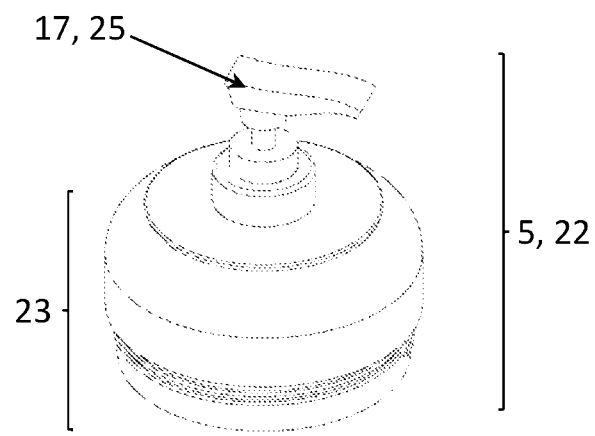
FIG. 7 is a view of the top portion of the container indicating the hollow compartment and where the opening is a pump.
Figure 8:
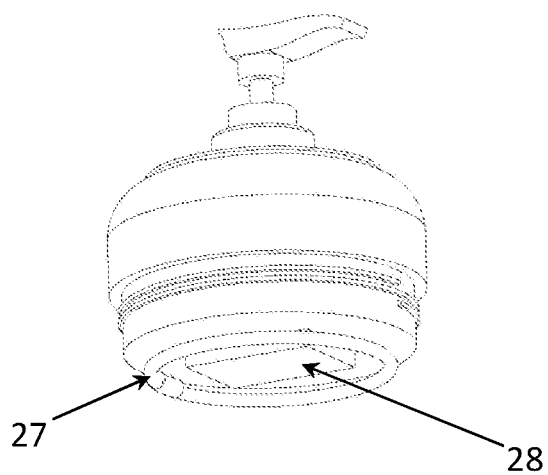
FIG. 8 is a view of the inside of the main compartment indicating the uv light and activation means.

The present disclosure reveals a container 1 with the appearance of an item such as but not limited to a shampoo bottle, a conditioner bottle, or a soap dispenser, for concealing an adult toy 2 so that the adult toy within the container can be inconspicuously transported and stored around the living environment, wherein the container 1 comprises a bottom portion 3, a main compartment 4 and a top portion 5. The personal hygiene item is defined as but not limited to a shampoo bottle, conditioning bottle, or soap dispenser.

In the first embodiment 6 of the container the container 1 comprises a bottom portion 3, a main compartment 4 and a top portion 5, wherein the bottom portion 3 has an upper part 7 and an underside 8 with an attachment 9 around the outside edge 10 of the upper part 7. The upper part 7 of the bottom portion further comprises a stand 11 to hold the adult toy 2 within the container 1.

The main compartment 4 of the first embodiment 6 has an upper edge 12, a lower edge 13 and a plurality of sides 14 wherein the plurality of sides 14 come together to form a closed geometric shape such as a cylinder, square, rectangle, pentagon, or other artistic shape in order to appear as a personal hygiene item, and the main compartment 4 is hollow so that the adult toy 2 can be concealed within the main compartment 4. The lower edge 13 of the main compartment 4 further comprises a receiver 15 to allow the main compartment 4 to be attached to the bottom portion 3. The upper edge 12 of the main compartment 4 further comprises a receiver 15 to allow the main compartment 4 to be attached to the top portion 5.

The top portion 5 of the first embodiment 6 has a lower edge 16 and what appears to be an opening 17, wherein the opening is a flip top or a pump. The lower edge 16 of the top portion 5 further comprises an attachment 9 to allow the top portion 5 to be attached to the main compartment 4.

In a second embodiment 18 of the bottom portion 3, wherein the bottom portion 3 further comprises a storage means 19 wherein the upper part 7 is attached to the storage means 19 by an appropriate means of attachment 20, the upper part 7 is removable from the storage means 19 and the storage means 19 can be filled with disposable wipes. The upper portion 7 of the bottom portion 3 also has an opening 21 such that the disposable wipes can be removed from the storage means 19 one at a time.

In a second embodiment 22 of the top portion 5 the top portion 5 further comprises a hollow compartment 23 within the top portion 5 to allow the top portion 5 to hold a liquid such as shampoo, conditioner, or soap. In the second embodiment 22 the opening 17 of the top portion comprises a flip top opening 24 or a pump means 25 to allow the user of the container 1 to extract liquid within the hollow compartment 23.

The container 1 may further comprise a uv light 27 with an activation means 28 such that, when the adult toy 2 is placed in the main compartment 4, the user activates activation means 28 of the uv light 27 the adult toy 2 is exposed to the uv light 27 for a period of time while in the container 1 before the uv light 27 automatically shuts off, in order to facilitate the sterilization of the adult toy 1.

The each of the disclosed embodiments, as well as the uv light 27, may each be individually included in the container 1 or the disclosed embodiments, as well as the uv light 27 may be included in any combination.

What is claimed:

1. A container with the appearance of a shampoo bottle, a conditioner bottle, or a soap dispenser, for concealing an adult toy so that the adult toy within the container can be inconspicuously transported and stored around the living environment comprising:
    a container to be used for concealing an adult toy;
    the container comprising a bottom portion, a main compartment and a top portion;
    the bottom portion comprising an upper part and an underside with an attachment around the outside edge of the upper part;
    the upper part of the bottom portion further comprising a stand to hold the adult toy within the container;
    the main compartment comprising an upper edge, a lower edge and in combination with the bottom portion and the top portion form a closed geometric shape, and is hollow so that the adult toy can be concealed within the main compartment;
    the lower edge of the main compartment further comprising a receiver to allow the main compartment to be attached to the bottom portion;
    the upper edge of the main compartment further comprising a receiver;
    the top portion comprising a lower edge and including an opening;
    said opening being at least one of a flip top or a pump; and
    the lower edge of the top portion further comprising an attachment to allow the top portion to be attached to the main compartment wherein the main compartment further comprises a uv light with an activation means such that, when the adult toy is placed in the main compartment, the user activates the activation means of the uv light and the adult toy is exposed to the uv light for a period of time while in the container before the uv light automatically shuts off, in order to facilitate the sterilization of the adult toy.

* * * * *